United States Patent
Brownscombe et al.

(10) Patent No.: US 6,355,834 B1
(45) Date of Patent: Mar. 12, 2002

(54) PROCESS FOR MAKING AN AROMATIC DIACID IN ONE STEP USING A SINGLE CATALYST SYSTEM

(75) Inventors: Thomas Fairchild Brownscombe; Susan Secor Pfrehm, both of Houston; William Larry King, Sugarland, all of TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/644,228

(22) Filed: Aug. 22, 2000

Related U.S. Application Data

(60) Provisional application No. 60/151,530, filed on Aug. 30, 1999.

(51) Int. Cl.$^7$ ............................................... C07C 51/16
(52) U.S. Cl. ..................................................... 562/412
(58) Field of Search ......................................... 562/412

(56) References Cited

U.S. PATENT DOCUMENTS

| | | |
|---|---|---|
| 4,931,572 A | 6/1990 | Saleh et al. |
| 5,329,058 A | 7/1994 | Shimada et al. |
| 5,510,563 A | 4/1996 | Smith et al. |

*Primary Examiner*—Paul J. Killos

(57) ABSTRACT

Disclosed is a process for manufacturing an aromatic diacid in one step with a single catalyst system which comprises:

a) Introducing into a reactor an aromatic hydrocarbon containing the number of rings desired in the product diacid with one or more alkyl groups attached to the rings;

b) Reacting said aromatic hydrocarbon in the presence of an oxidant supply and a single catalyst system comprising at least one catalyst selected from Group IB, IIB, VB, or VIIB of the Periodic Table, in a reaction medium capable of stabilizing the aromatic acids formed against further oxidation to water and $CO_2$, or decarboxylation to aromatic hydrocarbons, and also capable of allowing the isomerization of the acids so formed to the desired diacids; and c) Reacting said hydrocarbon feed with said oxidant in the presence of said catalyst system until a desired amount of said feed is oxidized to carboxylic acids and isomerized to the desired diacid product.

16 Claims, No Drawings

PROCESS FOR MAKING AN AROMATIC DIACID IN ONE STEP USING A SINGLE CATALYST SYSTEM

This application claims the benefit of U.S. Provisional Application No. 60/151,530, filed Aug. 30, 1999, the entire disclosure of which is hereby incorporated by reference.

FIELD OF INVENTION

This invention generally relates to oxidation and disproportionation/isomerization reactions. More particularly, this invention is related to catalysts, conditions, and media used to combine oxidation and disproportionation/isomerization reactions to form aromatic diacids. Still more particularly, this invention is a novel process for making aromatic diacids in one step from aromatic methyl compounds using a single catalyst system. The examples demonstrate the manufacture of 2,6-naphthalene dicarboxylic acid (2,6-NDA) in one step using the catalyst system of the present invention.

BACKGROUND OF THE INVENTION

Aromatic dicarboxylic acids are highly useful organic compounds. They are often used as monomers for the preparation of polymeric materials. 2,6-naphthalene dicarboxylic acid (2,6-NDA) is a particularly useful aromatic carboxylic acid, because it can be reacted with ethylene glycol to prepare poly(ethylene-2,6-naphthalate), PEN. Fibers and films manufactured from PEN display improved strength and superior thermal properties compared with other polyester materials such as polyethylene terephthalate. High strength fibers made from PEN can be used to make tire cords, and films made from PEN are advantageously used to manufacture magnetic recording tape and components for electronic applications.

All of the processes in the art for producing aromatic dicarboxylic acids, including 2,6-NDA, require multiple separate steps, including oxidation and isomerization. The catalyst for each of these steps is distinct and the catalysts for the various steps are incompatible.

Currently, the most common process for making 2,6-NDA starts with relatively expensive o-xylene and butadiene feedstocks, as discussed, for example, in U.S. Pat. No. 5,510,563 and U.S. Pat. No. 5,329,058. The 2,6-NDA is formed from the xylene and butadiene by a complex set of reactions terminating in a solid acid catalyzed isomerization of a family of dimethyl napthalene isomers to the 2,6-NDA form. The 2,6 dimethyl naphthalene is then oxidized to 2,6-NDA by means of a cobalt/manganese catalyst system in a liquid organic solvent. Besides the numerous steps, the process requires extensive purification.

In the 1970s Teijin briefly operated a type of Henkel process in which a dialkyl naphthalene was oxidized to 1,8-naphthoic dicarboxylic acid anhydride, or other naphthoic acid derivatives, using catalysts similar to those used in the second step of the process of U.S. Pat. No. 5,510,563 and U.S. Pat. No. 5,329,058. The acids were subsequently converted to potassium salts and isomerized in a disproportionation reaction using a completely different catalyst under a set of conditions distinct from previous steps.

It would constitute a vast improvement over anything currently available in the art if it were possible to effect isomerization and oxidation simultaneously, with one catalyst system. For example, this would make it possible to take a mixture of methyl naphthalenes or dimethyl naphthalenes, and convert them directly, using a single catalyst system in one step, to 2,6-NDA or its salts.

It is known in the art that catalysts other than cobalt/manganese will oxidize aromatic methyl groups to aromatic acids. For example, phthalic anhydride is commercially manufactured by air oxidation of ortho-xylene over vanadium pentoxide catalysts, usually supported on titania or other infusible supports. However, 2,6-NDA cannot be manufactured by this method, nor can terephthalic acid (TPA), since while phthalic anhydride (PA) is volatile (bp 163° C.) at the reaction temperature (typically near 300° C.), neither TPA nor 2,6-NDA is appreciably volatile, and, therefore, if a mixture of, for example, para-xylene and ortho-xylene is fed to the PA process, the result is PA from the ortho-xylene, and complete combustion or decarboxylation of the paraxylene, which is held up on the vanadia titania catalyst until it is burned to water and $CO_2$.

In the present invention we have unexpectedly discovered a method of addressing the deficiency characteristic of a vanadium catalyst in the $V_2O_5$ oxidation of para-substituted dimethyl aromatics, and have discovered a means for applying the use of a vanadium-containing catalyst system to the manufacture of 2,6-NDA from monomethyl naphthalenes. Furthermore, we have discovered a process for manufacturing 2,6-NDA in one step, using a single reactor.

SUMMARY

In accordance with the foregoing the present invention comprises:

A process for manufacturing an aromatic diacid in one step with a single catalyst system which comprises:
- a) Introducing into a reactor an aromatic hydrocarbon containing the number of rings desired in the product diacid with one or more alkyl groups attached to the rings;
- b) Reacting said aromatic hydrocarbon in the presence of an oxidant supply and a catalyst system comprising at least one catalyst selected from Group IB, IIB, VB, or VIIB of the Periodic Table, or a mixture thereof, in a reaction medium capable of stabilizing the aromatic acids formed against further oxidation to water and $CO_2$ or decarboxylation to aromatic hydrocarbons, and also capable of allowing the isomerization of the acids so formed to the desired diacids; and
- c) Reacting said hydrocarbon feed with said oxidant in the presence of said catalyst and medium system until a desired amount of said feed is oxidized to carboxylic acids and isomerized to the desired diacid product.

DETAILED DESCRIPTION OF THE INVENTION

The hydrocarbon feed in the present invention comprises one containing the aromatic rings desired in the final diacid, with one or more alkyl groups attached to the rings, in mixture or in single isomers. Hydrocarbons which are suitable as starting materials in the present invention include aromatic hydrocarbons containing one or more benzene rings, including, but not limited to benzene, toluene, xylene, and tetralin, and condensed aromatic hydrocarbons such as naphthalene, anthracene, phenanthrene, etc.,with one or more alkyl groups attached to the rings, or a mixture thereof, or a fraction containing one or more of them.

The catalyst used in the present invention comprises a compound selected from Group IB, IIB, VB, or VIIB of the Periodic Table. Suitable catalysts include compounds of vanadium, zinc, manganese, and cobalt in the form of, for example, oxides, halides, sulfates, carbonates, and carboxylates of these metals. Suitable vanadium catalysts include vanadium catalysts known in the art, including supported vanadium catalysts, as described, for example in U.S. Pat. No. 4,931,572, incorporated by reference herein in the entirety.

The vanadium metal oxide source may be vanadium pentoxide or may be a vanadium compound such as an ammonium metavanadate, vanadyl sulfate, vanadyl halide (e.g., vanadyl chloride, vanadyl dichloride), vanadyl oxyhalide (e.g., vanadyl oxychloride), metavanadic acid, pyrovanatic acid, vanadium hydroxide, and vanadyl carboxylates such as formate, tartrate, salicylate and oxalate, which can then become vanadium oxide at the calcining temperature.

Suitable zinc compounds include zinc halides such as zinc fluoride, zinc chloride, zinc bromide, and zinc iodide; zinc carboxylates such as zinc naphthoate and zinc naphthalenedicarboxylate; zinc oxide, zinc carbonate; zinc sulfate and mixtures thereof.

The preferred catalysts are vanadium pentoxide and zinc oxide.

The catalyst can optionally be on a support. Where the catalyst is on a support, the support may be selected from Groups II, III, IV, or V of the Periodic Table. Supported catalysts for use in either fixed or fluidized bed operations employ carriers including alumina, silica, silica gel, silica-alumina, silicon carbide, magnesium oxide, titania and titania-silica zirconia, zeolites such as zeolite Y as well as mixtures thereof. Where a support is used in the present invention, the preferred support is titania.

In the present invention it is desirable to employ a medium which is capable of stabilizing the aromatic acids formed against further oxidation to water and $CO_2$, or carboxylation to aromatic hydrocarbons, and also capable of allowing the isomerization of the acids so formed to the diacids. One suitable medium for stabilizing the aromatic diacids formed by the oxidation comprises a eutectic mixture.

A eutectic mixture provides the lowest melting point of a mixture of two or more alkali metals that is obtainable by varying the percentage of the components. Eutectic mixtures have a definite minimum melting point compared with other combinations of the same metals. For example, though the melting point of $Li_2CO_3$ is 622° C., in a eutectic mixture of alkali carbonates the melting point can be 400° C. What is preferred, where a eutectic mixture is employed, is the right mixture of alkali metal carbonates where the melting point is less than about 400° C. Generally the ratio of alkali metal carbonates in the eutectic mixture is about 1:1:1, but it can vary. One eutectic mixture successfully used as a medium was $K_2CO_3$, $Rb_2CO_3$, and $Cs_2CO_3$.

Many other media are available, however, and all have the characteristic of a high level of molecular mobility at some point in the temperature range generally desired for oxidation and isomerization, from about 300° C. to about 550° C.

What is necessary for a useful medium in the present invention is the ability to stabilize the aromatic acids formed against rapid decomposition to products other than the desired diacid (salts) under the reaction conditions. Therefore, preferred media are those capable of rapidly forming alkali metal salts, especially potassium salts, from the aromatic diacids formed by oxidation over the oxidation catalyst.

The preferred media will therefore be basic, with alkali metal cations, and capable of rapid reaction with the aromatic diacids. A large number of molten salt eutectics containing an excess of potassium bases could give the effect of the instant invention. Most preferred, however, will be those containing easily regenerated anions, such as carbonate, if recovery of the diacid is by acidification with $CO_2$. However, other means of recovery, such as precipitation of the diacid salt from solution or melt followed by a separate recovery step to remove the alkali metal cation, are feasible, and in such instances other anions may be desired in the oxidation/isomerization medium, as will be obvious to those skilled in the art.

In the practice of the instant invention, attention will also be paid to minimizing the overall cost of production. It is found, for example, that the alkali carbonate eutectics are only mildly corrosive to stainless steels, some hundreds of hours of operation being accompanied by insignificant metallographic changes. Other possible media, such as molten potassium hydroxide, however, are strongly corrosive to stainless steel, requiring high alloy reactors, which may be less preferred due to raising the cost of the overall process due to extra capital requirements.

It will be appreciated that the oxidation catalyst part of the medium, for example cobalt, vanadium, manganese, etc., may be present as discrete particles, or may in fact form a molten salt with the stabilization/isomerization medium. Vanadium pentoxide, for example, is known to form molten salt eutectics with basic alkali metal oxides and related compounds. It has been found in brief examination that either form of the oxidation catalyst is effective for the practice of the instant invention. A requirement of the instant invention, however, is the rapid effective stabilization of the aromatic acid oxidation product by the stabilization medium, so said medium must be in intimate proximity to the acids at their time of generation by oxidation. It will further be appreciated by those skilled in the art that intimate mixing of the oxidizing gas with the hydrocarbon feed and the catalyst(s) and stabilizing medium is preferred to increase the rate and productivity of the reaction. Such mixing may be obtained by various means, including but not limited, to effective stirring of a molten medium containing the reagents, contact of gases with a high surface area film of molten liquid or supported molten or a mobile medium on a solid support, injection of air and/or hydrocarbon into a bed of the medium, and catalyst flow of a mixture of air and hydrocarbon over solid particles, fluidized or not, containing the active ingredients for oxidation and stabilization, or by many other variations. For example, one could charge a reactor with a molten salt eutectic containing excess potassium base, oxidation catalyst, isomerization catalyst (e.g. ZnO), and fit it with a mechanical stirrer capable of vigorously mixing the contents with a vapor phase containing hydrocarbon, oxygen, and $CO_2$.

One could also support such a mixture on a support such as alumina, zirconia, titania, etc. and form a packed or fluidized bed, through which a gas stream of hydrocarbon feed, $CO_2$, and oxygen is directed. One could also operate either a bed or a molten salt medium with liquid phase hydrocarbon (at temperature below the critical point of the hydrocarbon), and gaseous oxidant. Those familiar with oxidations will recognize many other possible configurations to implement the instant invention.

Suitable reaction conditions for the one step manufacture of an aromatic diacid include a pressure in the range of from 100 psig to greater than 5000 psig. A more suitable range is from about 250 psig to 1000 psig, and a preferred range is from about 275 psig to 500 psig. A suitable temperature is from about 300° C. to about 550° C. A preferred range is from about 425 ° C. to about 475° C.

The following examples will serve to illustrate specific embodiments of the invention disclosed herein. These examples are intended only as a means of illustration and should not be construed as limiting the scope of the invention in any way. Those skilled in the art will recognize many variations that may be made without departing from the spirit of the disclosed invention.

EXAMPLE 1—COMPARATIVE

A 500 cc Hastelloy C reactor capable of operation at 5000 psig at 500° C. is outfitted with a high speed mechanical stirrer and a condenser capable of condensing methyl naphthalenes (jacketed at 100° C.) as well as a supply of high pressure oxygen/$CO_2$ gas mixture (90% $CO_2$, 10% $O_2$). (This gas mixture is thought to be generally incapable of forming an explosive mixture with any suitable hydrocarbon feed.) The autoclave is then charged with 250 g of a 1:1:1 molar ratio mixture of potassium, rubidium, and cesium carbonates, 20 g of 2-methyl naphthalene, pressured to 300 psig with the $O_2/CO_2$ mixture, and heated to 450° C. The reactor is stirred vigorously (about 2000 rpm) for 3 hours, and the heat turned off. On cooling, the contents are analyzed and found to contain no detectable 2,6-NDA. Some coupling reactions to produce heavier aromatic hydrocarbons have occurred.

EXAMPLE 2—COMPARATIVE

The experiment of Comparative Example 1 is repeated with $V_2O_5$ (20 cc) and 20 cc of hydrocarbon, without the eutectic medium. On termination of the reaction, much of the hydrocarbon has been destroyed by oxidation. Char, coke, and condensed hydrocarbons are found in the product. Extensive production of water is observed ($CO_2$ cannot be observed easily due to the $CO_2$ diluent). No 2,6-NDA is detected in the product.

EXAMPLE 3—INVENTIVE

The experiment of Comparative Example 1 is repeated with the addition of 10 g of $V_2O_5$ to the carbonate eutectic medium. On cooling the reactor and analyzing the contents, a 15% yield of NDAs is observed basis the hydrocarbon charged, primarily 2,6-NDA, as the alkali metal salt. A lesser amount of naphthoic acid salts is also observed. Analysis is conducted by nmr on the $D_2O$ salt solutions (in which $V_2O_5$ is found to be insoluble), and on the pure acids isolated by acidification of the aqueous salt solutions with selective precipitation of the 2,6-NDA.

EXAMPLE 4—INVENTIVE

The experiment of example 3 is repeated, with the addition of 10 g of ZnO as a catalyst to promote isomerization. A yield of NDAs of about 20% based on the hydrocarbon feed charged is observed, with a somewhat higher ratio of 2,6-NDA than in the above example.

EXAMPLE 5—INVENTIVE

A mixture of alkali metal carbonates and $V_2O_5$ is supported on alumina and charged with 20 cc of 2-methyl naphthalene into the autoclave used in the previous examples. Oxygen and $CO_2$ is flowed through the system as before, the hydrocarbon being retained by the condenser, but without mixing the contents. On stopping the reaction, naphthoic acids, naphthalene dicarboxylic acids, and 2,6-NDA salts are observed in the supported medium.

EXAMPLE 6—INVENTIVE

A small Hastelloy vessel is charged with 50 g of KOH and 5 g of $V_2O_5$, 5 g of 2-methyl naphthalene, and pressurized with the $O_2/CO_2$ mixture. On heating to 450° C. for 2 hours and cooling, naphthoic acids, naphthalene dicarboxylic acids, and 2,6-NDA are observed as their respective potassium salts.

EXAMPLE 7—INVENTIVE

The example of inventive example 1 is repeated, using a mixture of 1-methyl naphthalene and 2-methyl naphthalene. Essentially the same results are observed, with a yield of 15–20% of acid salts basis hydrocarbon.

EXAMPLE 8—INVENTIVE

The experiment of inventive example 1 is repeated using a mixture of monomethyl and dimethyl naphthalenes, with related results. Monomethyl naphthoic acids might be expected in the product, but if present, were present in small amounts, the major products being, as before, naphthoic acids and NDAs.

We claim:

1. A process for manufacturing an aromatic diacid in one step with a single catalyst system which comprises:
   a) Introducing into a reactor an aromatic hydrocarbon containing the number of rings desired in the product diacid with one or more alkyl groups attached to the rings;
   b) Reacting said aromatic hydrocarbon in the presence of an oxidant supply and a single catalyst system comprising at least one catalyst selected from Group IB, IIB, VB, or VIIB of the Periodic Table, or a mixture thereof, in a reaction medium capable of stabilizing the aromatic acids formed against further oxidation to water and $CO_2$ or decarboxylation to aromatic hydrocarbons, and also capable of allowing the isomerization of the acids so formed to the desired diacids; and
   c) Reacting said hydrocarbon feed with said oxidant in the presence of said catalyst system until a desired amount of said feed is oxidized to carboxylic acids and isomerized to the desired diacid product.

2. The process of claim 1 wherein said aromatic hydrocarbons are selected from compounds of benzene and naphthalene containing one or more alkyl groups attached to the rings.

3. The process of claim 1 wherein the oxidant is selected from oxygen and air.

4. The process of claim 3 further comprising the oxidant containing a diluent.

5. The process of claim 4 wherein the diluent is $CO_2$ sufficient to avoid operation at conditions susceptible to explosion.

6. The process of claim 1 wherein the catalyst is selected from one or more compounds of zinc, cobalt, manganese and vanadium.

7. The process of claim 6 wherein the catalyst is selected from vanadium pentoxide and zinc oxide.

8. The process of claim 1 wherein the medium in which the catalyst is present is a eutectic mixture.

9. The process of claim 8 wherein the eutectic mixture is selected from one or more alkali carbonates.

10. The process of claim 9 wherein the eutectic mixture is $K_2CO_3$, $Rb_2CO_3$, and $Cs_2CO_3$.

11. The process of claim 1 further comprising a stirring sufficient to ensure contact of said hydrocarbon with the supplied oxidant phase.

12. The process of claim 1 further comprising heating and cooling said reactor to maintain a specific temperature.

13. A method for adapting a vanadium oxide catalyst to manufacture aromatic dicarboxylic acids which comprises using said catalyst with a medium which is capable of stabilizing the aromatic acids formed against oxidation to water and $CO_2$ or decarboxylation to aromatic hydrocarbons, and also capable of allowing the isomerization of the acids so formed to the desired diacids.

14. The process of 13 wherein the medium comprises a eutectic mixture.

15. The process of 14 wherein the eutectic mixture comprises $K_2CO_3$, $Rb_2CO_3$, and $Cs_2CO_3$.

16. The process of claim 1 further comprising the catalyst is optionally on a support.

* * * * *